United States Patent [19]

Sugo et al.

[11] Patent Number: 4,897,433
[45] Date of Patent: Jan. 30, 1990

[54] PROCESS FOR PRODUCING AN ANTI-THROMBOGENIC MATERIAL BY GRAFT POLYMERIZATION

[75] Inventors: Takanobu Sugo; Jiro Okamoto; Seiryo Tasaki, all of Gunma; Tadayuki Onishi, Kanagawa, all of Japan

[73] Assignees: Japan Atomic Energy Research Inst.; Sumitomo Bakelite Co., Ltd., both of Tokyo, Japan

[21] Appl. No.: 129,319

[22] Filed: Dec. 3, 1987

[30] Foreign Application Priority Data

Dec. 8, 1986 [JP] Japan ................................. 61-292246
Jun. 9, 1987 [JP] Japan ................................. 62-142138
Jul. 10, 1987 [JP] Japan ................................. 62-172439

[51] Int. Cl.$^4$ ............................ C08J 3/28; C08J 7/16; C08J 7/18; C08L 51/06
[52] U.S. Cl. ...................................... 522/116; 427/2; 427/35; 427/36; 427/44; 428/35.7
[58] Field of Search ................... 522/116, 149; 428/35; 427/541, 12, 35, 36, 2, 44

[56] References Cited

U.S. PATENT DOCUMENTS

| | | | |
|---|---|---|---|
| 4,196,065 | 4/1980 | Gaussens et al. | 522/144 |
| 4,377,010 | 3/1983 | Fydelor et al. | 428/451 |
| 4,717,741 | 1/1988 | Hainfeld et al. | 522/116 |

OTHER PUBLICATIONS

*Covalent Binding of Biomolecules to Radiation-Grafted Hydrogels or Inert Polymer Surfaces,* Trans. Amer. Soc. Artif. Int. Organs 1972, Hoffman et al.; pp. 10–17.
Antithrombogenic Material with Diffuse Layer, Ikada, Y. *Jpn. J. Artif. Organs* 15(1) 12–15 (1986).
Blood-Compatibility-Water-Content Relationships for Radiation-Grafted Hydrogels, B. D. Radner et al., Journal of Polymer Science Polymer Symposium 66, 363–375 (1979).
Article by A. Nakao et al., *Jpn. J. Artif. Organs,* 13(3), 1151–1154 (1984).

*Primary Examiner*—Allan M. Lieberman
*Attorney, Agent, or Firm*—Browdy and Neimark

[57] ABSTRACT

A process for producing a medical material having high anti-thrombogenicity that is suitable for use in catheters and other medical devices in contact with blood flowing in circulatory organs and other tissues is disclosed. According to this process, an acrylamide or methacrylamide derivative having a tertiary amino group, or an unsaturated monomer having a hydrophihlic group and the ability to promote copolymerization, or a mixture thereof is graft polymerized onto a polyurethane elastomeric or polyolefinic high-molecular weight substrate with an ionizing radiation.

3 Claims, No Drawings

PROCESS FOR PRODUCING AN ANTI-THROMBOGENIC MATERIAL BY GRAFT POLYMERIZATION

BACKGROUND OF THE INVENTION

The present invention relates to a process of producing an anti-thrombogenic material. More particuarly, the present invention relates to a process for producing a medical material having high anti-thrombogenicity by grafting a hydrophilic monomer onto a high-molecular weight substrate.

A variety of high-molecular weight materials have been used as medical materials. However, these material are foreign to living organisms and if they are used in direct contact with blood, they induce blood coagulation and cause occlusion or deposition of blood clot. These are highly undesirable phenomena that impair the capabilities of these high-molecular weight materials when used in medical devices. Therefore, a strong need exists to develop anti-thrombogenic materials that will not induce blood coagulation.

Various approaches have been taken in the efforts toward developing anti-thrombogenic medical materials. One of the methods under review is to support anticoagulants on high-molecular weight materials. However, the amount of anticoagulants that can be supported by this method is limited and, in addition, the short life of available anticoagulants makes it unrealistic to anticipate prolonged anti-thrombogenic effects. In an attempt at imparting anti-thrombogenicity to high-molecular weight materials per se, the idea of introducing a macro-domain dispersive structure has been investigated. This method is effective in preventing the activation of deposited platelets and coagulation factors but is not equally effective against already activated blood; in other words, the efficacy of this method is not consistent.

In order to prevent blood coagulation, it is most effective to prevent the occurrence of physiochemical interactions between coagulation factors in the blood and high-molecular weight substrates. The walls of blood vessels in living organisms have carbohydrate chains on the surfaces of their cell membranes that exhibit similar effects in preventing interactions with blood. Methods based on this idea have been proposed by Hoffman et al. (Trans. Amer. Soc. Artif. Int. Organs, 1972, Vol. XVIII, pp 10-17) and Ikada et al. (Jinko Zoki, 15, 1, pp 12-15, 1986) and consist of forming highly hydrophilic and mobile polymer chains on the surface of a high-molecular weight substrate, thereby constructing a diffuse surface that prevents interactions between living tissues and the substrate. The efforts directed to those methods center on techniques that employ graft polymerization and many monomers including 2-hydroxyethyl methacrylate (HEMA) and acrylamide (AAm) have been reviewed as candidate grafts. The results of such reviews are described in prior patents such as Japanese Patent Publication Nos. 32554/1975, 15556/1978 and 43563/1982, and Unexamined Published Japanese Patent Application Nos. 72294/1979, 5320/1983 and 45328/1984.

However, the methods disclosed in these patents are all directed to the formation of a hydrogel layer. Hydrogels have a large amount of water confined in cross-linked polymer chains and their mechanical strength is comparatively low. Furthermore, the mobility of the polymer chains is not necessarily high and their interactions with blood components are not completely eliminated [see B. D. Ratnar et al., J. Polym. Sci.: Polym. Symp., 66, 363-375 (1979) and A. Nakao et al., Jinko Zoki, 13, 3, pp 1151-1154 (1984)]. Therefore, in order to construct an effective diffuse surface having high anti-thrombogenicity, efficient formation of a long chain of polymers in a highly hydrated state is desired and it is necessary to avoid undue deterioration of physical strength. Preclinical studies have been conducted with a view to constructing anti-thrombogenic surfaces by graft polymerization and improved anti-thrombogenicity data from animal experiments have been reported (K. Hayashi et al., Kobunshi Ronbunshu, vol. 39, pp 179-182, 1982, and vol. 42, pp 77-83, 1985). Therefore, graft polymerization holds most promise as a technique for constructing anti-thrombogenic surfaces.

SUMMARY OF THE INVENTION

The present inventors conducted various studies in order to prepare anti-thrombogenic materials by application of graft polymerization. As a result, the present inventors found that a very high degree of anti-thrombogenicity could be attained by performing graft polymerization of a (meth)acrylamide derivative with a tertiary amino group on a high-molecular weight substrate. An object, therefore, of the present invention is to provide a medical material having a very high degree of anti-thrombogenicity that is adapted for use in catheters and other medical devices in contact with blood flowing in circulatory organs and other living tissues.

The present invention has been accomplished on the basis of the finding described above. In accordance with this invention, a material having high anti-thrombogenicity can be produced by performing graft polymerization of a (meth)acrylamide derivative with a tertiary amino group and/or a hydrophilic monomer with a copolymerization accelerating property on a polyolefinic or polyurethane elastomeric high-molecular weight substrate.

DETAILED DESCRIPTION OF THE INVENTION

The (meth)acrylamide derivative having a tertiary amino group that is used in the present invention is a monomer having a polymerizable carbon-carbon double bond. Upon graft polymerization, this monomer is introduced into a high-molecular weight substrate as it forms graft chains which construct a diffuse layer on the substrate so as to exhibit anti-thrombogenicity. This monomer is highly hydrophilic and hydrated because it contains a tertiary amino group and an amido group, which are both hydrophilic, in its molecule. Therefore, graft chains composed of this monomer have high affinity for water and form an effective diffuse layer. This monomer may be exemplified by (meth)acrylamides having introduced therein alkylamines that have been rendered tertiary by a methyl group, which include, for example, N,N-dimethylaminopropylacrylamide, N,N-diethylaminopropylacrylamide, N,N-dimethylaminopropylmethacrylamide, and N,N-diethylaminopropylmethacrylamide.

In the present invention, the above-defined hydrophilic aminic (meth)acrylamide based monomer may be used in combination with a hydrophilic monomer having the ability to promote graft polymerization of said aminic (meth)acrylamide based monomer. This second monomer, when subjected to co-graft polymerization in a solution containing a mixture of said monomer with the first monomer, forms graft chains together with the first monomer, thereby allowing it to be introduced in an increased amount. Forming graft chains from the combination of the two monomers has the additional advantage that the hydrophilicity of the monomer having the ability to accelerate copolymerization contributes to the materialization of the hydrophilicity of the (meth)acrylamide having a tertiary amino group; this serves to form a more effective diffuse surface that has enhanced anti-thrombogenicity. Specific examples of the hydrophilic monomer having a copolymerization accelerating effect are acrylate-, methacrylate- and vinyl-based monomers having a hydrophilic group, and exemplary hydrophilic groups include polyoxyethylene, alcohol, glycol and amido groups. Illustrative monomers that are effective in providing further enhanced anti-thrombogenicity during co-graft polymerization include (meth)acrylates having a polyoxyethylene group whose degree of polymerization is 2–10, (meth)acrylates having a hydrocarbon based hydrophilic group with no more than 3 carbon atoms into which an alcoholic or glycolic hydroxyl group has been introduced, and hydrophilic monomers having an amino structure. More specific examples include: methoxytetraoxyethylene (meth)acrylate, methoxynonaoxyethylene (meth)acrylate, hydroxyethyl (meth)acrylate, dihydroxypropyl (meth)acrylate, acrylamide, and N-vinylpyrrolidone.

A monomer represented by the general formula shown below has the advantage that the surface of a polyolefinic high-molecular weight substrate can be provided with anti-thrombogenicity by homo-graft polymerization of said monomer that consists of exposing said substrate to an ionizing radiation and subsequently immersing the irradiated substrate in a solution of said monomer:

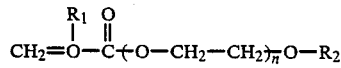

where $R_1$ is H or $CH_3$; $R_2$ is $CH_3$ or $C_2H_5$; and n is an integer of 2–20.

The monomer represented by this general formula is a methyl- or ethyl-terminated acrylate or methacrylate derivative having a polyethylene glycol group. This monomer is introduced in a substrate by forming graft chains through graft polymerization. In order for the introduced graft chains to form an anti-thrombogenic surface, the interfacial free energy of the substrate must be lowered by forming a diffuse surface layer of said graft chains. The monomer defined above has a polyethylene glycol group which is a nonionic hydrophilic group and the terminal hydroxyl group is alkylated. Therefore, this monomer offers a small degree of ionic interactions with blood and the formation of hydrogen bonds with the molecule of water is reduced to a sufficiently low level to retain loose coupling that depends chiefly upon hydrophilic-hydrophobic interactions with the molecule of water. In addition, this monomer has a small degree of reactivity for crosslinking and, unlike the hydroxyethyl methacrylate, acrylamide and other monomers employed in the Comparative Examples to be described later in this specification, this monomer hardly undergoes popcorn polymerization and other reaction that lead to the formation of a crosslinked polymer. Having these characteristics, the monomer represented by the above-noted formula is best suited for the formation of a diffuse surface layer.

A further advantage of this monomer is that since the polyethylene glycol group itself is a polymer, hydrophilic groups having an increased chain length can be produced that are anticipated to increase the interfacial mobility of graft chains, thereby preventing the deposition of blood clot. However, excessively long chains of hydrophilic groups are undesirable since the increase in the molecular weight of the monomer itself causes a decrease in the concentration of vinyl group that contribute to graft polymerization, which leads to a lower efficiency of graft polymerization. If the chain length of hydrophilic groups is short, the efficiency of graft polymerization is high but, on the other hand, a high degree of hydrophilicity is not attained. Therefore, the preferred chain length of the polyethylene glycol group is such that n is the general formula of the monomer under discussion is in the range of 2–20, with the range of 4–10 being more preferred.

The high-molecular weight substrate to be used in the present invention serves as a support in which graft chains are to be introduced by graft polymerization. Any high-molecular weight compound that can be subjected to graft polymerization is useful in the present invention but polyolefinic and polyurethane based high-molecular weight compounds which are highly susceptible to graft polymerization are desirable. Polyolefinic high-molecular weight compounds are those which are chiefly formed of carbon-carbon bonds and may be exemplified by polyethylene, polypropylene and polybutadiene that are produced by various methods. Copolymers with olefinic monomers into which substituents such as tetrafluoroethylene have been introduced can also be used. Polyurethane based high-molecular weight compounds are those which are chiefly formed of urethane bonds. Various types of polyurethane are known and may be used in the present invention so long as they can be subjected to graft polymerization. Thermoplastic polyurethane elastomers are preferred since they are highly susceptible to graft polymerization and will not substantially impair the mobility of the graft chains produced.

The graft polymerization to be performed in the present invention is such a process that after active sites are produced in the high-molecular weight chain of substrate polyolefin or polyurethane by a certain method, a polymerizable monomer is allowed to react with said active sites, thereby forming graft chains at the active sites so as to introduce the monomer in the substrate. Active sites can be produced by various known methods such as a chemical method employing a reagent such as a cerium salt, a method using an activated gas such as ozone or plasma, and a physical method employing light or an ionizing radiation. Any of these methods may be employed in the present invention so long as they permit for subsequent graft polymerization. However, the method using an ionizing radiation is preferred from the viewpoint of activation efficiency and transmissivity. Useful ionizing radiations include beta-rays, gamma-rays, X-rays, neutron rays, and accelerated particle beams such as accelerated electron beams.

To attain the principal feature of the present invention (i.e., high anti-thrombogenicity), it is important to make highly hydrophilic and mobile graft chains in an efficient manner. To this end, allowing the monomer in solution to react with active sites on the high-molecular weight substrate is a desired method because, for one thing, the homopolymerization of the monomer and the crosslinking of the graft chains produced can be reduced by proper selection of the reaction solvent and the temperature of the monomer and, for another, any homopolymer that is formed can be washed away after the reaction.

Radiation-initiated graft polymerization may be performed by irradiating the substrate either prior to the addition of a monomer or in its presence. While both methods can be employed in the present invention to achieve graft polymerization, the best method is desirably selected depending upon the properties of the high-molecular weight substrate and the monomer.

The monomer solution should be selected for each reaction system since optimum conditions for such factors as the monomer concentration, monomer composition and the solvent greatly vary with the composition and shape of the substrate. Generally speaking, the monomer concentration is desirably reduced to 50% and less in order to inhibit the occurrence of homopolymerization. A suitable solvent for the monomer solution is selected from among water, alcohols, ketones, etc.

The present invention relates to a process for producing a medical material having high anti-thrombogenicity. The medical material provided by the present invention is useful as the material of tubes, sheets, catheters, cannulas, implant biomaterials, artificial blood vessels, artificial organs and other devices to be used in contact with blood.

The following examples are provided for the purpose of further illustrating the present invention but are in no way to be taken as limiting.

EXAMPLE 1

Low-density polyethylene films (50 μm thick) were exposed to electron beams for a total dose of 30 Mrad in a nitrogen atmosphere. Therefore, the irradiated films were immersed in solutions of monomers A, B and C in closed glass containers in a nitrogen atmosphere, and subjected to graft polymerization in a thermostated water bath at 45° C. After the passage of predetermined times, the glass containers were opened and the recovered films were washed and dried under vacuum. The graft level of each film was calculated by measuring the difference between the weight of the grafted film and its initial weight. The results are shown in Table 1. All of the grafted films were clear and smooth-surfaced.

TABLE 1

| Monomer | General formula of monomer | Monomer solution composition | Reaction time (hr) | Graft level (%) | Sample No. |
|---|---|---|---|---|---|
| A | $R_1 = R_2 = CH_3$ <br> $n = 4$ | 80% aqueous solution | 2 <br> 8 | 5 <br> 18 | 1 <br> 2 |
| A | $R_1 = R_2 = CH_3$ <br> $n = 4$ | 80% ethanol solution | 1 <br> 3 | 16 <br> 39 | 3 <br> 4 |
| B | $R_1 = R_2 = CH_3$ <br> $n = 9$ | 80% ethanol solution | 8 <br> 22 | 2.2 <br> 3.5 | 5 <br> 6 |
| C | $R_1 = R_2 = CH_3$ <br> $n = 23$ | 30% ethanol solution* | 8 <br> 22 | 0.8 <br> 0.9 | 7 <br> 8 |

*High monomer concentration was unattainable since monomer C was solid and had low solubility.

COMPARATIVE EXAMPLE 1

Low-density polyethylene films (50 μm thick) were exposed to electron beams for a total dose of 20 Mrad in a nitrogen atmosphere. Thereafter, the films were immersed in solutions of 2-hydroxyethyl methacrylate (HEMA) and acrylamide (AAm) in a nitrogen atmosphere in closed glass containers and subjected to graft polymerization in a thermostated water bath at 25° C. (HEMA) or 40° C. (AAm). After the passage of predetermined times, the glass containers were opened and the recovered films were washed with water and dried under vacuum. The graft level of each film was calculated by measuring the difference between the weight of the grafted film and its initial weight. The results are shown in Table 2. The HEMA-grafted films turned opaque and had a structure composed of spherical particles with a size of several microns. The AAm-grafted films were clear but had asperities on their surface.

TABLE 2

| Monomer | Monomer structural formula | Monomer solution composition | Reaction time (hr) | Graft level (%) | Sample No. |
|---|---|---|---|---|---|
| HEMA | $CH_2{=}C(CH_3){-}C({=}O){-}OCH_2CH_2OH$ | 20% aqueous solution | 1 <br> 5 | 24 <br> 170 | 9 <br> 10 |
| AAm | $CH_2{=}CH{-}C({=}O){-}NH_2$ | 20% aqueous solution | 2 <br> 6 | 42 <br> 189 | 11 <br> 12 |

ASSAYING ANTI-THROMBOGENICITY

The percent production of blood clot on the grafted films was measured by the Imai method according to the following procedures. A mixture of fresh rabbit ACD blood (250 μl) and 0.8% CaCl$_2$ (25 μl) was held between two sheets of a sample, which were placed on a thermostated bath (37° C.) to start blood coagulation. For each measurement, a medical polyvinyl chloride sheet was used as a control and the clotting time was set at such a value that the level of production of blood clot on the control would be 50–80% of complete clotting. In order to eliminate the possible difference in clotting ability between measurements, the percent production of clot was determined in relative values by dividing the weight of a clot formed on a test sample by the weight of a clot formed on the control. The results are shown in Table 3.

TABLE 3

| Sample No. | Monomer | Graft level (%) | Relative clot formation (%) |
|---|---|---|---|
| 3 | A | 16 | 16 ± 6 (n = 4) |
| 4 |  | 39 | 26 ± 10 (n = 4) |
| 9 | HEMA | 24 | 70 ± 4 (n = 3) |
| 10 |  | 170 | 58 ± 14 (n = 3) |
| 11 | AAm | 42 | 86 ± 23 (n = 4) |
| 12 |  | 189 | 56 ± 16 (n = 4) |
| Substrate | LDPE | — | 101 ± 44 (n = 4) |
| Control | Medical PVC | — | 100 |

ASSAYING THE STICKINESS OF PLATELETS

PRP (platelet rich plasma) was prepared from fresh rabbit blood and placed in contact with a test sample for 10 minutes at 37° C. Thereafter, the sample was washed with physiological saline, fixed with glutaraldehyde, washed with ethanol and Giemsa-stained. The number of platelets adherent on the surface of the sample was counted under an optical microscope (×1000). The adherent platelet counts were expressed in terms of relative values, with the value for the ungrafted low-density polyethylene film being taken as 100. The results are shown in Table 4.

TABLE 4

| Sample No. | Monomer | Graft level (%) | Adherent platelet count (%) |
|---|---|---|---|
| 3 | A | 16 | ≦10 |
| 4 | A | 39 | ≦10 |
| 9 | HEMA | 24 | 60 |
| 11 | AAm | 42 | 40 |
| Substrate | LDPE | 0 | 100* |

*The number of adherent platelets was ca. 22,000 per mm$^2$.

EXAMPLE 2

A low-density polyethylene film (50 μm thick) was exposed to accelerated electron beams (acceleration voltage, 2.0 MeV; irradiation current, 1 mA) for a total dose of 20 Mrad in a nitrogen atmosphere. Thereafter, the film was immersed in a solution of 80% N,N-dimethylaminopropylacrylamide (DMAPAA of Kohjin Co., Ltd.) in ethanol in a nitrogen atmosphere in a closed glass container and subjected to graft polymerization for 6 hours in a thermostated water bath at 40° C. After the polymerization, the film was recovered from the glass container, washed thoroughly with pure water and methanol and subsequently dried under vacuum.

The grafted film was clear and smooth-surfaced, with a graft level of 14.8%. The grafted film was immersed in water for 48 hours at room temperature and the amount of water absorbed was divided by the weight of the graft polymer in the film to determine the percent water absorption of the film. The anti-thrombogenicity of the film was assayed by the Imai method in accordance with the following procedures. A mixture of fresh rabbit ACD blood (250 μl) and 0.8% CaCl$_2$ (25μl) was held between two sheets of the sample, which were placed in a water-vapor saturated petri dish on a thermostated water bath (37° C.) to start blood coagulation. For each measurement, a medical polyvinyl chloride sheet was used as a control and the clotting time was set at such a value that the level of production of blood clot on the control would be 50-80% of complete clotting. The percent production of clot was determined in relative values by dividing the weight of a clot formed on the test sample by the weight of a clot formed on the control. The results are shown in Table 5.

EXAMPLE 3

A low-density polyethylene film (50 μm thick) was irradiated with gamma-rays from cobalt-60 for 3 hours at a dose rate of 0.1 Mrad/hr while it was immersed in a solution of 60% DMAPAA in ethanol in a nitrogen atmosphere in a closed glass container. After the reaction, the film was recovered from the glass container, washed thoroughly with pure water and methanol and dried under vacuum.

The grafted film was clear and smooth-surfaced, with a graft level of 9.2%. The percent water absorption and anti-thrombogenicity of the sample were measured as in Example 2. The results are shown in Table 5.

COMPARATIVE EXAMPLE 2

Low-density polyethylene films (50 μm thick) were exposed to accelerated electron beams (acceleration voltage, 1.5 MeV; irradiation current, 1 mA) for a total dose of 10 Mrad in a nitrogen atmosphere. Thereafter, the films were immersed in an aqueous solution of 2-hydroxyethyl methacrylate (HEMA of Kishida Chemical Co., Ltd.) in a nitrogen atmosphere in closed glass containers and subjected to graft polymerization on a thermostated water bath (25° C.) for different periods of time. After the reaction, the films were recovered from the glass containers, washed thoroughly with methanol and pure water, and subsequently dried under vacuum.

The graft level of the samples was 6.7% for the reaction time of 2 hours, 44.3% for 2 hours and 79.6% for 4 hours. As the graft level increased, the film surface roughened and at the graft level of 79.6%, the film turned opaque. The percent water absorption and anti-thrombogenicity of the samples were measured as in Example 2. The results are shown in Table 5.

COMPARATIVE EXAMPLE 3

Low-density polyethylene films (50 μm thick) were exposed to accelerated electron beams (accelerated voltage, 2.0 MeV; irradiation current, 1 mA) of a total dose of 20 Mrad in a nitrogen atmosphere. Thereafter, the films were immersed in a solution of 20% acrylamide (AAm) in a mixture of water and acetone (1:4) in a nitrogen atmosphere in closed glass containers and subjected to graft polymerization on a thermostated water bath (40° C.) for different periods of time. After the reaction, the films were recovered from the glass containers, washed thoroughly with methanol and pure water, and subsequently dried under vacuum.

The graft level of the samples was 28.5% for the reaction time of 1 hour, 80.2% for 2 hours, and 153.8% for 4 hours. As the graft level increased, the film surface roughened but the films retained their transparency. The percent water absorption and anti-thrombogenicity of the samples were measured as in Example 2. The results are shown in Table 5.

TABLE 5

| Sample | Graft monomer | Graft level (%) | Water absorption (%) | No. of measurements | Relative clot formation (%) |
|---|---|---|---|---|---|
| Ex. 2 | DMAPAA | 14.8 | 73 | 4 | 17 ± 12 |
| Ex. 3 | " | 9.2 | 23 | 4 | 52 ± 22 |
| Comp. Ex. 2 | HEMA | 6.7 | 2 | 4 | 77 ± 13 |
| Comp. | " | 44.3 | 14 | 4 | 108 ± 26 |

TABLE 5-continued

| Sample | Graft monomer | Graft level (%) | Water absorption (%) | No. of measurements | Relative clot formation (%) |
|---|---|---|---|---|---|
| Ex. 2 | | | | | |
| Comp. Ex. 2 | " | 79.6 | 10 | 6 | 90 ± 28 |
| Comp. Ex. 3 | AAm | 28.5 | 16 | 4 | 114 ± 59 |
| Comp. Ex. 3 | " | 80.2 | 38 | 4 | 80 ± 16 |
| Comp. Ex. 3 | " | 153.8 | 30 | 4 | 65 ± 17 |

EXAMPLE 4

Polyurethane sheets (polyether type; 100 μm in thickness) were subjected to graft polymerization as in Example 2. The graft level of the samples was 9.3% for the irridation time of 1.5 hours and 13.2% for 3 hours. The samples were all smooth-surfaced. The percent water absorption and anti-thrombogenicity were measured as in Example 2. The results are shown in Table 6.

COMPARATIVE EXAMPLE 4

Polyurethane sheets (polyether type; 100 μm in thickness) were subjected to graft polymerization as in Example 2 except that a solution of 15% HEMA in ethanol was used as a monomer solution. The graft level of the samples was 10.6% for the irradiation time of 0.5 hours, 27.8% for 1 hour and 151.0% for 3 hours. The samples were all smooth-surfaced. The percent water absorption and anti-thrombogenicity were measured as in Example 2. The results are shown in Table 6.

COMPARATIVE EXAMPLE 5

Polyurethane sheet (polyether type; 100 μm in thickness) was subjected to graft polymerization as in Example 2 except that a solution of 20% AAm in ethanol was used as a monomer solution. The graft level of the sample was 7.7% for the irradiation time of 2 hours. Because of the crystallization of a homopolymer, the film turned opaque in several areas. The percent water absorption and anti-thrombogenicity were measured as in Example 2. The results are shown in Table 6.

COMPARATIVE EXAMPLE 6

Polyurethane sheet (polyether type; 100 μm in thickness) were exposed to accelerated electron beams (acceleration voltage, 1.5 MeV; irradiation current, 1 mA) for a total dose of 30 Mrad in a nitrogen atmosphere. Thereafter, the sheets were immersed in a solution of 30% AAm in a mixture of water and ethanol (1:1) in a nitrogen atmosphere in closed glass containers and subjected to graft polymerization on a thermostated water bath at 40° C. After the reaction, the substrate sheets were recovered from the glass containers, washed thoroughly with pure water and methanol, and dried under vacuum.

The graft level of the samples was 18.4% for the irradiation time of 0.5 hours, and 36.9% for 1.5 hours. The samples were all smooth-surfaced. The percent water absorption and anti-thrombogenicity were measured as in Example 2. The results are shown in Table 6.

TABLE 6

| Sample | Graft monomer | Graft level (%) | Water absorption (%) | No. of measurements | Relative clot formation (%) |
|---|---|---|---|---|---|
| Ex. 4 | DMAPAA | 9.3 | 148 | 4 | 26 ± 8 |
| " | " | 13.2 | 151 | 4 | 4 ± 3 |
| Comp. Ex. 4 | HEMA | 10.6 | 44 | 4 | 101 ± 39 |
| Comp. Ex. 4 | " | 27.8 | 37 | 4 | 109 ± 17 |
| Comp. Ex. 4 | " | 151.4 | 41 | 4 | 64 ± 17 |
| Comp. Ex. 5 | AAm | 7.7 | 78 | 3 | 99 ± 21 |
| Comp. Ex. 6 | " | 18.4 | 63 | 4 | 136 ± 56 |
| Comp. Ex. 6 | " | 36.9 | 92 | 4 | 168 ± 51 |

EXAMPLE 5

Polyurethane (Tecoflex 85A of Thermedics Inc., USA) was extrusion-molded to form a tube having an outside diameter of 7 mm and an inside diameter of 5 mm. The inner surface of this tube was subjected to graft polymerization as in Example 3. A graft level of 17.3% was attained by irradiation for 3 hours.

The anti-thrombogenicity of this tube was assayed by the following procedures. The grafted tube was bent in a U shape and submerged in a thermostated water bath (37° C.) with both ends being above the water level. A 1-ml sample of fresh whole rabbit blood was injected into the tube at one end to start blood coagulation. A measurement was started at the time of blood sampling. The tube was inclined at given intervals of time and the time when the blood in the tube ceased to flow was used as the whole blood clotting time. In some samples, the blood continued to flow without forming any adherent clot on the inner tube surface even when coagulation had occurred. As for such samples, the blood was taken from within the tube at given time intervals and checked for the presence of any clot. A U-shaped glass tube was used as a control sample. A U-shaped glass tube having a coating of Biomer ® (Ethicon Corp. USA) on the inner surface was also used as a control.

COMPARATIVE EXAMPLE 7

Polyurethane tubes of the same type as used in Example 5 were subjected to graft polymerization as in Example 3 except that a solution of 20% HEMA in ethanol and a solution of 30% AAm in ethanol were used as monomer solutions. The HEMA graft level was 84.5% for the irradiation time of 4 hours, and the AAm graft level was 7.0% for 0.5 hours. Anti-thrombogenicity measurements were conducted as in Example 5. The results are shown in Table 7.

TABLE 7

| Sample | Graft level (%) | Total blood clotting time (min) | Stop of blood flow | Remarks |
|---|---|---|---|---|
| Glass | | 10 | yes | |
| Biomer ® (cast on glass tube) | | 33 | yes | |
| Polyurethane | | 30 | yes | |
| DMAPAA-grafted tube | 17.3 | >90 | no | ca. 40% clotting after 90 minutes |
| HEMA-grafted | 84.5 | 24 | yes | |

TABLE 7-continued

| Sample | Graft level (%) | Total blood clotting time (min) | Stop of blood flow | Remarks |
|---|---|---|---|---|
| tube AAm-grafted tube | 7.0 | 26 | yes | |

EXAMPLE 6

Polyurethane sheets (polyether type; 100 μm in thickness) were immersed in solutions of monomer mixtures (for their composition, see Table 8) in a nitrogen atmosphere in closed glass containers and subjected to graft polymerization by irradiating them with gamma-rays from cobalt-60 for predetermined periods of time at a dose rate of 0.1 Mrad/hr. After the reaction, the substrate sheets were recovered from the glass containers, repeatedly washed with pure water and methanol, and dried under vacuum.

The grafted samples were weighed and their total graft level was calculated by the following formula:

$$\text{Total graft level (\%)} = \frac{\text{weight after graft polymerization} - \text{weight before graft polymerization}}{\text{weight before graft polymerization}} \times 100$$

The partial graft levels for N,N-dimethylaminopropylacrylamide (DMAPPAA) and other monomers were calculated by the following formula:

$$\text{DMAPAA graft level (\%)} = \text{total graft level} \times \frac{\text{DMAPAA content}}{\text{weight after graft polymerization} - \text{weight before graft polymerization}}$$

Graft level for other monomer (%) = total graft level − DMAPAA graft level.

The content of DMAPAA was measured by non-aqueous titration with a solution of 0.1N perchloric acid and acetic acid after a sample was dissolved in tetrahydrofuran and mixed with acetic acid in an amount of 3% (v/v) of tetrahydrofuran. A solution of Methyl Violet in acetic acid was used as an indicator and the point when a color change from red purple to blue purple occurred was used as the end point.

Anti-thrombogenicity assay was conducted by the Imai method according to the following procedures. A mixture of fresh rabbit ACD blood (250 μl) and 0.8% CaCl$_2$ (25 μl) was held between two sheets of a sample, which were placed in a water-vapor saturated petri dish on a thermostated water bath (37° C.) to start blood coagulation. Thereafter, the weight of a blood clot produced was measured. For each measurement, a medical polyvinyl chloride sheet was used as a control and the clotting time was set at such a value that the level of production of blood clot on the control would be 50–80% of complete clotting. Anti-thrombogenicity was expressed in terms of relative percent clot production, which was obtained by dividing the weight of a clot formed on a test sample by the weight of a clot formed on the control.

The composition of monomer solutions used in graft polymerization, irradiation times, total and partial graft levels of the grafted samples, and the data for relative clot formation are shown in Table 8, in which all values of monomer concentration are expressed in w/w%.

COMPARATIVE EXAMPLE 8

Graft polymerization was carried out as in Example 6 except that solutions containing DMAPAA as the sole monomer were employed as monomer solutions. Graft and anti-thrombogenic levels were also measured as in Example 6. The results are summarized in Table 8.

COMPARATIVE EXAMPLE 9

Graft polymerization was carried out as in Example 6 except that the monomer solution contained methoxytetraoxyethylene methacrylate (M40G), hydroxyethyl methacrylate (HEMA), acrylamide (AAm) or N-vinyl-pyrrolidone (NVP) as the sole monomer. Graft and anti-thrombogenicity levels were also measured as in Example 6. The results are summarized in Table 8.

High graft levels were difficult to attain with monomer solutions that contained DMAPAA as the sole monomer (Comparative Example 8) and, in order to attain high anti-thrombogenic levels, high monomer concentrations of at least 60% were necessary. However, by performing co-graft polymerization of DMAPAA with hydrophilic monomers having the ability to accelerate copolymerization as in Example 6, the DMAPAA graft level was increased with the attendant advantage that high anti-thrombogenic levels could be easily attained. The effectiveness of this co-graft polymerization is also evident from the comparison between samples prepared in Example 6 and those prepared is Comparative Example 8 which attained equivalent DMAPAA graft levels.

EXAMPLE 7

Polyurethane of the medical polyether type was extrusion-molded to form a tube having an outside diameter of 7 mm and an inside diameter of 5 mm. The inner surface of this tube was subjected to graft polymerization as in Example 6 using a solution of 15% DMAPAA and 20% M40G in ethanol. By 5-hour reaction, a grafted tube having a total graft level of 22.5%, a DMAPAA graft level of 7.5% and an M40G graft level of 15.0% was produced.

Whole blood clotting time was measured on this grafted tube by the following method. The tube was submerged in physiological saline overnight, bent in a V shape, and placed in a thermostated water bath (37° C.) with both ends of the tube above the water level. A 1-ml sample of whole rabbit blood was injected into the tube immediately after the blood sampling and the V-shaped tube was tilted at intervals of 2 minutes so as to check when the blood had ceased to flow. The same measurement was conducted on three control samples: a glass tube, a glass tube coated with Biomer ® on its inner surface, and a substrate polyurethane tube, all these tubes being in a V shape.

Blood coagulated and ceased to flow in 8 minutes in the glass tube, in 32 minutes in the Biomer ® coated glass tube, and in 30 minutes in the polyurethane tube. On the other hand, blood did not coagulate in the grafted tube even after the passage of 90 minutes; the blood taken out of the tube had coagulated by only about 30%. The deposition of blood clots on the inner surface of the grafted tube was negligible.

TABLE 8

| Sample | Monomer 1 (concentration in w/w %) | Monomer 2 (concentration in w/w %) | Reaction time (hr) | Total graft level (%) | Partial graft level (%) monomer 1/monomer 2 | Relative clot formation (%) |
|---|---|---|---|---|---|---|
| Ex. 6 | DMAPAA (30) | M40G (10) | 5.0 | 13.5 | 7.6/5.9 | (n = 4) 16 ± 10 |
| " | DMAPAA (30) | HEMA (10) | 4.0 | 27.7 | 13.9/13.8 | (n = 4) 4 ± 2 |
| " | DMAPAA (30) | AAm (15) | 2.0 | 10.7 | 7.1/3.6 | (n = 4) 6 ± 3 |
| " | DMAPAA (30) | NVP (10) | 3.0 | 13.2 | 10.8/2.4 | (n = 3) 21 ± 11 |
| Comp. Ex. 8 | DMAPAA (30) | — | 5.0 | 1.2 | — | — |
| Comp. Ex. 8 | DMAPAA (40) | — | 5.0 | 2.7 | — | (n = 4) 81 ± 49 |
| Comp. Ex. 8 | DMAPAA (60) | — | 1.0 | 9.3 | — | (n = 4) 26 ± 8 |
| Comp. Ex. 8 | DMAPAA (60) | — | 3.0 | 13.2 | — | (n = 4) 4 ± 3 |
| Comp. Ex. 9 | — | M40G (10) | 1.0 | 7.8 | — | (n = 4) 65 ± 15 |
| Comp. Ex. 9 | — | HEMA (15) | 1.0 | 27.8 | — | (n = 4) 109 ± 17 |
| Comp. Ex. 9 | — | AAM (10) | 0.5 | 4.9 | — | (n = 3) 185 ± 51 |
| Comp. Ex. 9 | — | NVP (20) | 3.0 | 3.3 | — | (n = 4) 159 ± 31 |

Note:
Ethanol was used as a reaction solvent.
DMAPAA: N,N—dimethylaminopropylacrylamide;
M40G: methoxytetraoxyethylene methacrylate;
HEMA: hydroxyethyl methacrylate;
AAm: acrylamide;
NVP: N—vinylpyrrolidone

What is claimed is:

1. A process for producing an anti-thrombogenic material in which
   an acrylamide or methacrylamide selected from the group consisting of N,N-dimethylaminopropylacrylamide, N,N-diethyl aminopropylacrylamide, N,N-dimethylaminopropylmethacrylamide and N,N-diethylaminopropylmethacrlamide, and
   a copolymerization promotor of at least one unsaturated monomer selected from the group consisting of an acrylate or methacrylate having an oligooxyethylene group whose degree of polymerization is 2–10, an acrylate or methacrylate having a hydrocarbon group with no more than 3 carbon atoms into which an alcoholic or glycolic hydroxyl group has been introduced, and acrylamide and N-vinylpyrrolidone
   are graft polymerized with an ionizing radiation onto a high-molecular weight substrate comprising a polyurethane elastomeric polymer or a polyolefinic polymer.

2. A process for producing an anti-thrombogenic material which comprises generating active sites on a polyurethane elastomeric or polyolefinic high-molecular weight substrate by treatment with an ionizing radiation, and immersing the treated substrate in a solution of an acrylamide or methacrylamide having a tertiary amino group selected from the group consisting of N,N-dimethylaminopropylacrylamide, N,N-diethylaminopropylacrylamide, N,N-dimethylaminopropylmethacrylamide and N,N-diethylaminopropylmethacrylamide, so as to effect graft polymerization.

3. A process for producing an anti-thrombogenic material which comprises immersing a polyurethane elastomeric high-molecular weight substrate in a mixed solution of
   an acrylamide or methacrylamide selected from the group consisting of N,N-dimethylaminopropylacrylamide, N,N-diethyl aminopropylacrylamide, N,N-dimethylaminopropylmethacrylamide and N,N diethylaminopropylmethacrylamide, and
   a copolymerization promotor of at least one unsaturated monomer selected from the group consisting of an acrylate or methacrylate having an oligooxyethylene group whose degree of polymerization is 2–10, an acrylate or methacrylate having a hydrocarbon group with no more than 3 carbon atoms into which an alcoholic or glycolic hydroxyl group has been introduced, an acrylamide and N-vinylpyrrolidone, and
   applying an ionizing radiation to effect co-graft polymerization.

* * * * *